(12) United States Patent
Hecht (10) Patent No.: US 11,331,210 B2
(45) Date of Patent: May 17, 2022

(54) POSTURE IMPROVING APPARATUS

(71) Applicant: Marlen Hecht, New York, NY (US)

(72) Inventor: Marlen Hecht, New York, NY (US)

(*) Notice: Subject to any disclaimer, the term of this patent is extended or adjusted under 35 U.S.C. 154(b) by 381 days.

(21) Appl. No.: 14/998,414

(22) Filed: Jan. 4, 2016

(65) Prior Publication Data
US 2018/0153727 A1    Jun. 7, 2018

(51) Int. Cl.
*A61F 5/02* (2006.01)

(52) U.S. Cl.
CPC .............. *A61F 5/026* (2013.01); *A61F 5/028* (2013.01); *A61F 5/024* (2013.01)

(58) Field of Classification Search
None
See application file for complete search history.

(56) References Cited

U.S. PATENT DOCUMENTS

| | | | | |
|---|---|---|---|---|
| 2,632,178 A * | 3/1953 | Kennedy | ................... | A61F 5/03 2/267 |
| 4,524,763 A * | 6/1985 | Eberling, Jr. | ........ | A61H 1/0229 482/142 |
| 5,062,414 A * | 11/1991 | Grim | ....................... | A61F 7/007 602/19 |
| 5,188,586 A * | 2/1993 | Castel | ..................... | A61F 5/028 128/845 |
| 5,950,628 A * | 9/1999 | Dunfee | ................. | A61F 5/0118 128/874 |
| 6,209,135 B1 * | 4/2001 | Irvin | .................. | A63B 21/0603 2/102 |
| 6,364,851 B1 * | 4/2002 | Nafpliotis | ............ | A63B 21/065 602/19 |
| 6,692,413 B1 * | 2/2004 | Greenberg | ......... | A41D 13/0012 2/108 |
| 9,456,919 B2 * | 10/2016 | Pollack | .................... | A61F 5/026 |
| 2011/0277212 A1 * | 11/2011 | Jones | ................. | A41D 13/0005 2/102 |
| 2015/0040286 A1 * | 2/2015 | Schultz | .................... | A41D 1/00 2/88 |

* cited by examiner

*Primary Examiner* — Ophelia A Hawthorne
(74) *Attorney, Agent, or Firm* — Ingenium Patents LLC; Peter R. Kramer (57) ABSTRACT

An Apparatus for realigning and improving the posture of the user. The Apparatus targets specific areas of the body, lifts up those areas, and then cause other specific areas of the body with the help of gravity, to adjust and modify, and facilitate the loosening and releasing of targeted fascia tissue, connective tissue, muscles, without the use or creation of force or tension, facilitating realignment, resulting in improving posture.

The Apparatus is comprised of Holding Areas (e.g. pockets, grooves, etc.) configured to run up and down the apparatus the length of the spine of the human body. The Holding Areas (e.g. pockets, grooves, etc.) are an integral part of the apparatus and/or a separate attachable unit to the apparatus. The Apparatus's Holding Areas (e.g. pockets, grooves, etc.) are of adjustable materials, and are filled, empty, or selectively filled with a choice of different types of fillers, inserts. The Apparatus is used on a flat surface or bed, or configured to be worn as a garment on a person. The Apparatus is utilized by the person in a lying down position, resting, or sleeping position.

17 Claims, 8 Drawing Sheets

Figure # 1  Back View of Posture Apparatus

Figure # 2   Back View of Posture Apparatus

Figure # 3  Back View of Posture Apparatus

Figure # 4 Back View of Posture Apparatus

Figure # 5 Back View of Posture Apparatus

FIG. 6

Figure #7 Back and Front view of Posture Apparatus

Figure # 8   Back View of Posture Apparatus

POSTURE IMPROVING APPARATUS

BACKGROUND OF INVENTION

Today's modern technology increases the incidence of "forward head", and "pulled forward neck" posture; as we text from our smart phones, tap on our lap tops, sit all day in offices and prolong sitting at our desk top computers, we are unconsciously leaning our heads forward. As the head leans forward, the resulting tension and sometimes pain causes the body to compensate with even worse posture and misalignment. We are experiencing an epidemic of slouching, rounded shoulders, stiff neck, pinched nerves, bad posture, and other physical ailments.

The bombardment of constant daily stresses is causing the upper body to tighten up. When your head and neck sag forward, that weight then pulls your shoulders forward and out of alignment and they get rounded. Your chest muscles are contracting and this contributes to shallow breathing. With this shallower breathing your body is not sufficiently oxygenated and a toxic internal environment results.

The resulting poor posture of the spine has been associated with many health problems, such as: tension headaches, increased blood pressure, osteoarthritis, herniated discs, pinched nerves, poor balance, etc. It even has been shown to compromise the body systems that rely on the proper functioning of the Sympathetic Nervous system, (endocrine, immune, digestive, etc.).

The faulty posture is also causing some degree of excessive forward curvature of the upper back. This also causes the "dead weight" of the head, and neck to lean forward over the chest instead of on top of the shoulders supported by the spinal column. This unbalanced head position increases the tendency of the head to fall forward, adding extra weight that needs to be supported and the neck to bend with it; And thus the neck muscles get strained and tightened and have a deleterious effect on the spine.

Bad posture resulting in the misalignment of the back is not only causing back and neck pain but also a wide range of other physical and emotional illnesses. And a hunched-over upper body position of poor posture can add years to one's appearance, and remove years from your life.

The importance of good posture is well known among health professionals. Posture generally refers to the alignment of the body and, more specifically, to the relative static and dynamic positioning of the body and its limbs. In a body exhibiting good posture, the spine has no lateral curvature and the legs have little angulation in the knees and ankles.

In addition, when viewed from the side, a healthy spine forms a slight S-shape with the two curves of the S-shape being evenly disposed on opposite sides of an imaginary line extending downwardly from the head through the body's center. Such an alignment provides an even distribution of body weight over the spine and lower body joints resulting in a relatively uniform distribution of pressure on the intervertebral discs of the spine.

The effects of poor posture are well documented and include limited range of motion wherein muscles, such as the pectoral muscles in the chest may be shorted due to a hunched-over upper body position.

Maintaining an awareness of proper posture may train certain muscles through muscle memory such that proper posture eventually becomes a habit. However, it is often difficult to maintain this active awareness of proper posture while engaged in other mental and physical activities such as using a smart phone, working at a computer, carrying heavy things and even a more passive activity such as watching television.

There have been many approaches to try to adjust and realign the body and improve posture.

Physical therapists may utilize postural therapy to improve the posture of a patient. Such postural therapy may include techniques such as shoulder taping, massage, and breathing exercises, etc. Conventional chiropractic techniques may utilize body manipulation and treatment to help keep the patient's spine in alignment. However, the patient must take the time and energy to visit the offices of a physical therapist or a chiropractor in order to receive the needed postural therapy and/or chiropractic manipulation. And often this therapy supplies pain relief but the adjustments do not often last very long.

Pillows such as chiropractic, cervical, memory, therapeutic, and contour pillows are shaped to accommodate the contours of the head and neck.

Pillows try to eliminate sore and stiff neck problems caused by sleeping incorrectly. They try to realign the head and neck by providing support to those areas. They are also used for medical issues in order to hold the body in a specific position. They have distinct designated areas where to place the head and neck, and changing body positions is not easy or helpful. Head and neck movement outside of these designated areas could cause more problems.

There are devices that try to realign the spine, In U.S. Pat. No. 8,252,024B2. the device is used as a guide to the placement of the spine. Two tubes run along both sides of the spine in order to form a specific indented area, a "gutter", "trough" for the spine placement and to sink into, which aids the user to determine if proper alignment of the spine has been reached.

There are other devices where the person rests their head and/or back on the device and inflates the pump with air that then applies upward pressure on the spine, to change the spines position.

There are devices designed for users who have existing injury or posture problems—the devices tend to be very tight, constraining and cumbersome and function as a "brace" for repairing or immobilizing the problem area.

There are also "posture support" and "posture correcting" devices that are worn during the day during activities and are meant to alert the wearer that their posture is off and to straighten up—though that doesn't mean that correct posture is then obtained. Some of these devices are also visibly noticeable and therefore wearing them is not a private matter.

U.S. Pat. Nos. 8,808,212, 7,578,798, 8,047,893, 7,871,388B2 are worn during the day and focus on creating tension to pull the shoulders back and in some cases also pulling the shoulders down. There are many variations on these designs but in general they comprise of straps, bands, loops, elastic, and fasteners, and materials that contribute to exerting and creating some measure of tension and force. They encircle the torso, and/or shoulders and have variations as to how they are put on and how they are tightened and where the tension, force is created. Some of these devices are very uncomfortable and the tension and restrictive nature of the device can throw off the alignment of other areas. Often these apparatus devices can't progressively adjust in accordance with improvements and changes in the user's posture over time.

To improve posture and adjust and realign the body these apparatuses/devices are primarily used while awake. Through tension, pressure, constraints, braces, that adjust the body they also often require the user to actively respond and to actively straighten and correct their posture.

These apparatus and devices don't focus on/and or allow the human body to retrain fascia tissue, muscles, and connective tissues, to facilitate better posture, without the use and the action of tension creating materials, force, braces or constraints, These apparatuses/devices don't counter the daily stresses on the posture, by encouraging the natural ability of the human body to correct itself during the optimum time for healing which is while sleeping and/or resting.

SUMMARY OF INVENTION

The Posture Improving Apparatus invention is a device for helping realign and improve the posture of the user. It is an apparatus device configured to target specific areas of the body, lift up and or modify those areas, that then cause other specific areas of the body, with the assistance of gravity, to adjust, modify, and facilitate the loosening and releasing of targeted fascia tissue, connective tissue, and muscles, without the use or creation of force or tension, and facilitate realignment, resulting in improving posture.

The Apparatus structure is configured to run up and down the back and/or front of the human body for the length of the spine or a portion of the spine. The Apparatus is expandable and contractible. The Apparatus is structured with Holding Areas (e.g. pockets, grooves, etc.). The Holding Areas (e.g. pockets, grooves, etc.) of the Apparatus are an integral part of the apparatus, and/or are a separate attachable unit and/or a self-contained unit. The Holding Areas (e.g. pockets, grooves, etc.) run up and down the back and/or front of the entire surface or in and on specific areas of the Apparatus. It is configured of lightweight and comfortable materials that are expandable, stretchable and non-stretchable.

The Holding Areas (e.g. pockets, grooves, etc.) have insert areas for fillers, inserts, lifts, etc., and are filled with a choice of various types of filler. The Holding Area (e.g. pockets, grooves, etc.), can be of different shapes and sizes, and are made of flexible, expandable, stretchable and non-stretchable material. The Holding Areas have the flexibility to be selectively filled or empty, with a choice of location, type of filler, size, width, depth, height, and length, etc.

The Apparatus is to be used on a flat surface or in bed while lying down, sleeping or resting and accommodates freedom of movement. We spend at least ⅓ of our time sleeping; And one of the benefits of, and medically acknowledged for optimum times for healing is while sleeping and resting.

By lifting up specific areas along the spine from the neck down, the Apparatus device counteracts the stretching and weakness of upper and mid back extensors (in the rib cage/thoracic spine region), which are the large group of back muscles that pull the spine erect and oppose the bending forward action of front abdominal muscles and the weight of the head. The Apparatus device counter acts the widening of the distance between shoulder blades, which causes widening and weakening of the Rhomboids and middle and lower Trapezius—the muscles that anchor the shoulder blades in back to the thoracic spinal column. The Apparatus device helps counteract the adaptive shortening and tightness of the front chest muscles—pectoralis major, and gently opens up the ribcage and chest cavity for deeper breathing and better health.

DESCRIPTION OF THE DRAWINGS

FIG. 1 Is a back view of the Posture Improving Apparatus (A). The posture improving apparatus is illustrated in FIG. 1 as one piece from the neck down to the end of the spine. (B) is illustrating holding areas, (e.g. pockets, grooves, etc.) (C) is illustrating openings/closures for the filler, lifts, and inserts to be put into. (D) is illustrating fasteners in different locations of the apparatus for adjustable extensions. (E) is illustrating side fasteners used for adjustment for desired fit.

FIG. 3 is attached to the apparatus, and can also be a self-contained separate unit that attaches to the Posture Improving Apparatus. Illustration (B) are markers for specific areas, e.g. spine, fascia tissue areas, muscle groups, etc. to determine placement of filler, inserts, lifts. Illustration (C) are markers to measure desired length and width of filler, inserts, lifts. (D) illustrates markers and/or fasteners for the user for proper alignment of the apparatus on the body. (E) illustrates grooves for the placement of the filler, inserts, lifts. (F) illustrates the fasteners for adding adjustable extensions.

FIG. 7 illustrates the back view of the neck attachment (A) as one piece or (B) separate pieces that can fasten to each other to lengthen the neck collar and (C) fasteners to attach to the Posture Apparatus. (D) illustrates the opening/closures for filler, lifts, inserts. FIG. 7 illustrates the front view of the neck attachment (E) is open with adjustable fasteners giving the option to keep the neck attachment open or closed.

Figure 1:
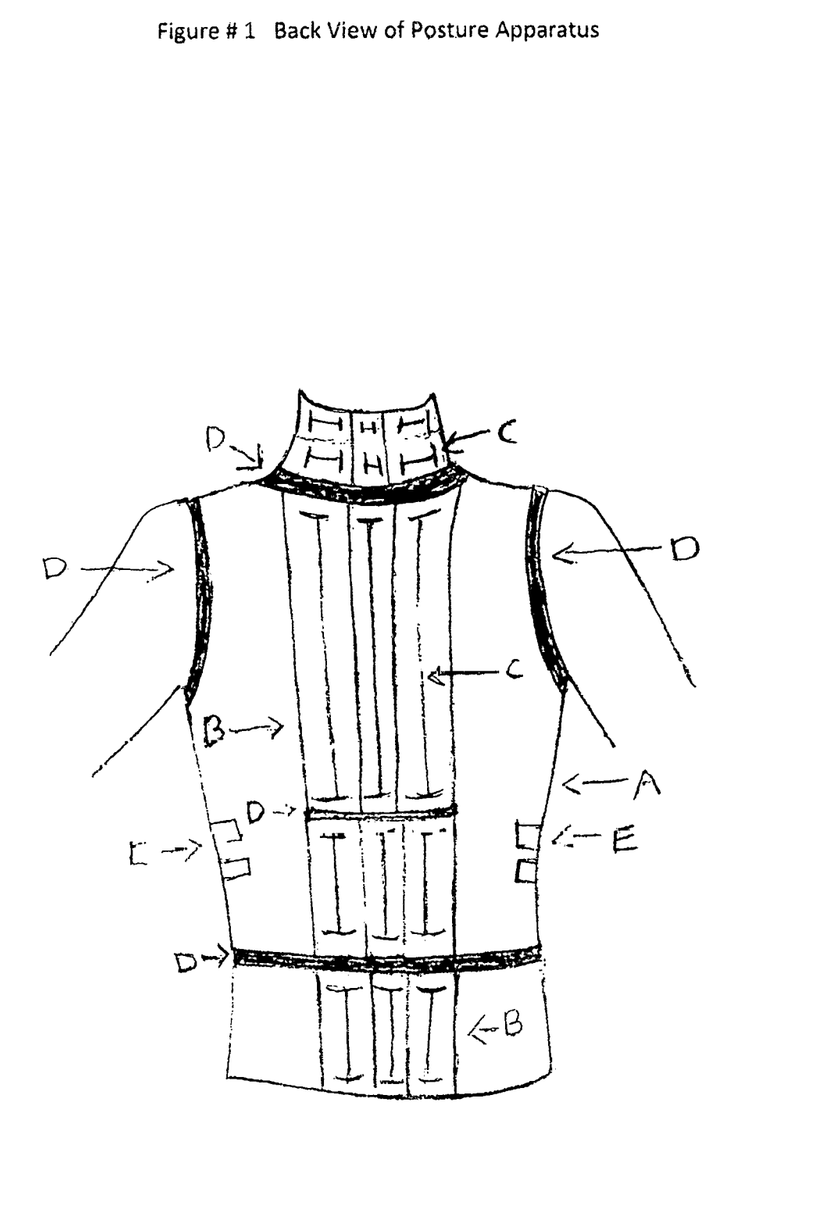
Figure 2:
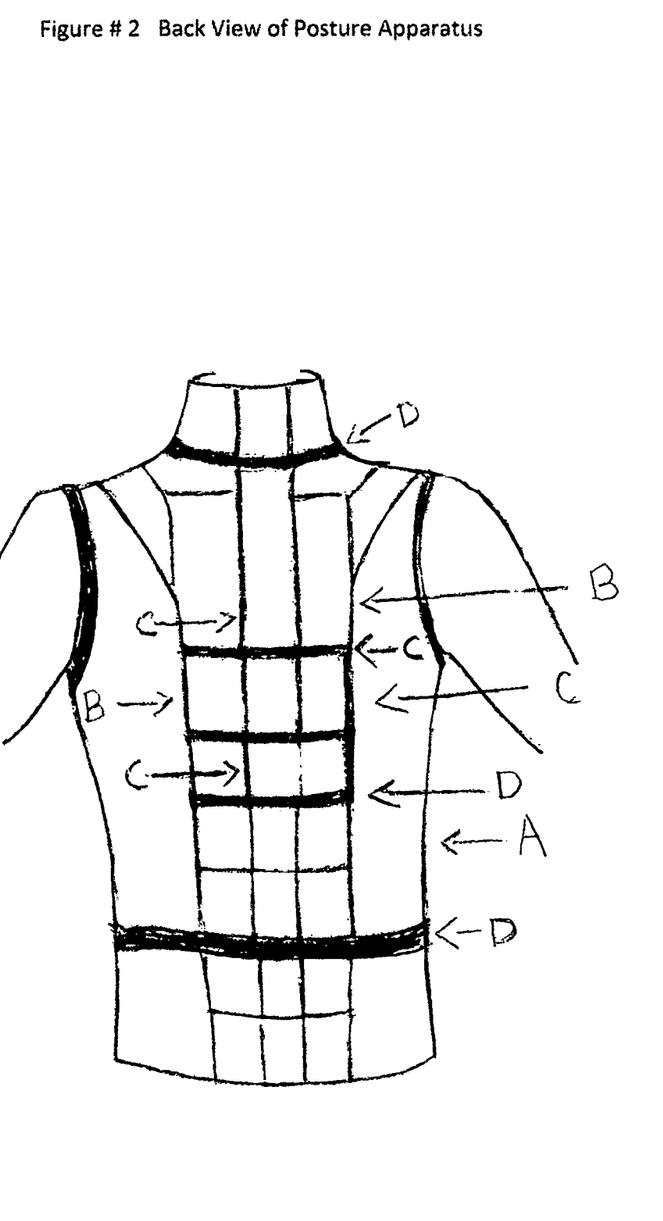
FIG. 2 Further comprises the back view of the Posture Improving Apparatus (A). where (B) holding areas, (e.g. pockets, grooves, etc.) are different sizes and shapes. The openings and closures for fillers, lifts, inserts (C) are different than FIG. 1 (B). They run horizontally and/or vertically either for individual holding areas (e.g. pockets, grooves, etc.) or groups of holding areas (e.g. pockets, grooves, etc.) The fasteners (D) are for separate adjustable extensions.
Figure 3:
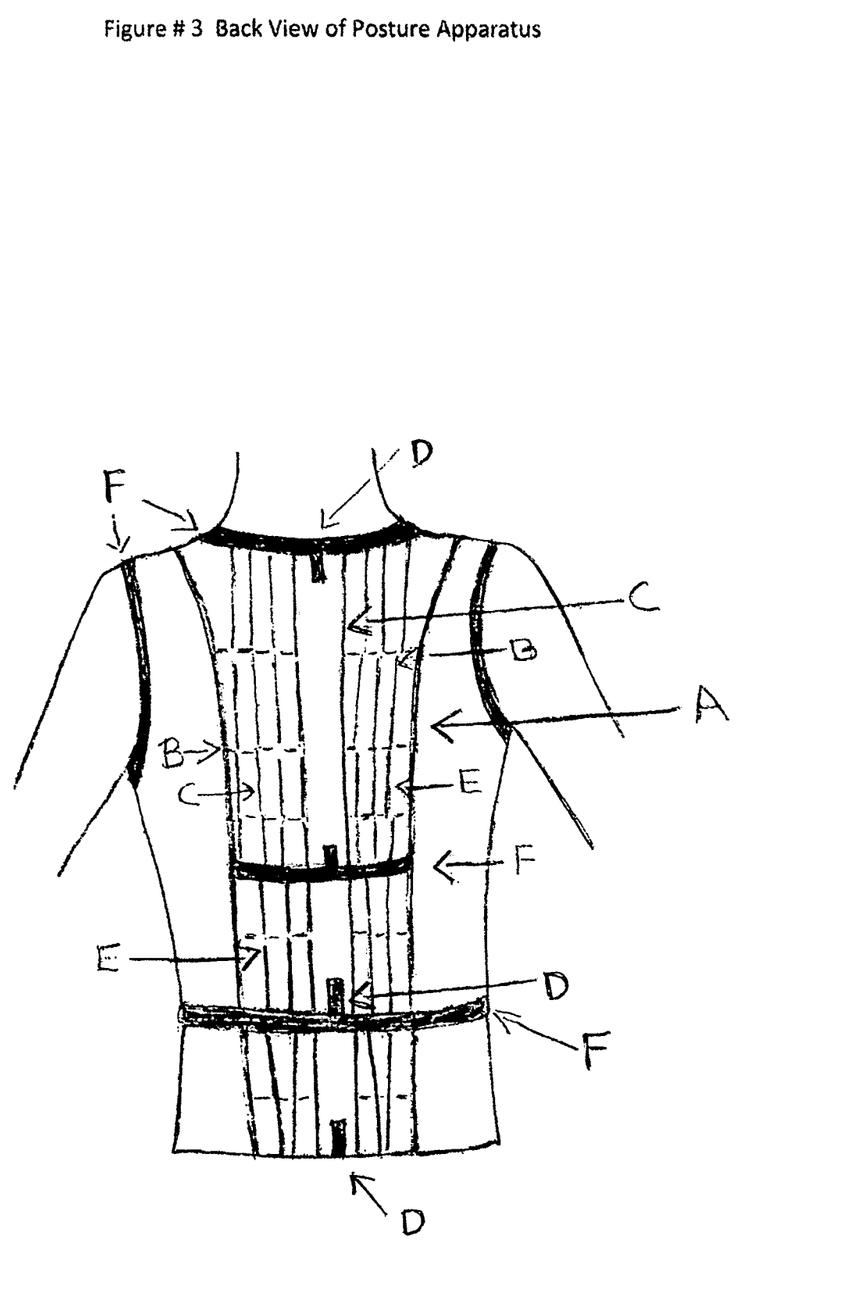
FIG. 3 Further comprises holding area (e.g. pockets, grooves, etc.) that are open and part of the apparatus and have individual closing fasteners or can be secured in place with overlay material illustrated in FIG. 4.
Figure 4:
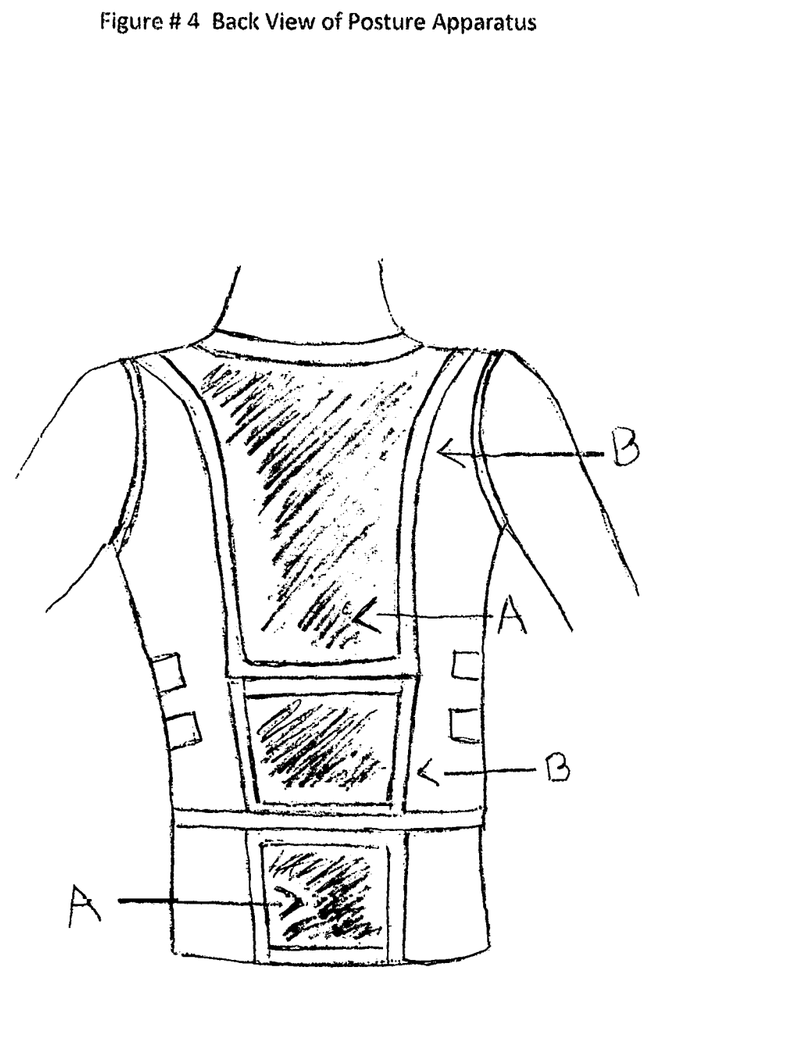
FIG. 4 Illustrates the back view of the holding area (e.g. pockets, grooves, etc.) as described in FIG. 3 and further comprises with an overlay material (A) that folds over the holding area (e.g. pockets, grooves, etc.). The overlay holds the filler, lifts, inserts in place. Fasteners (B) run the perimeter of the overlay.
Figure 5:
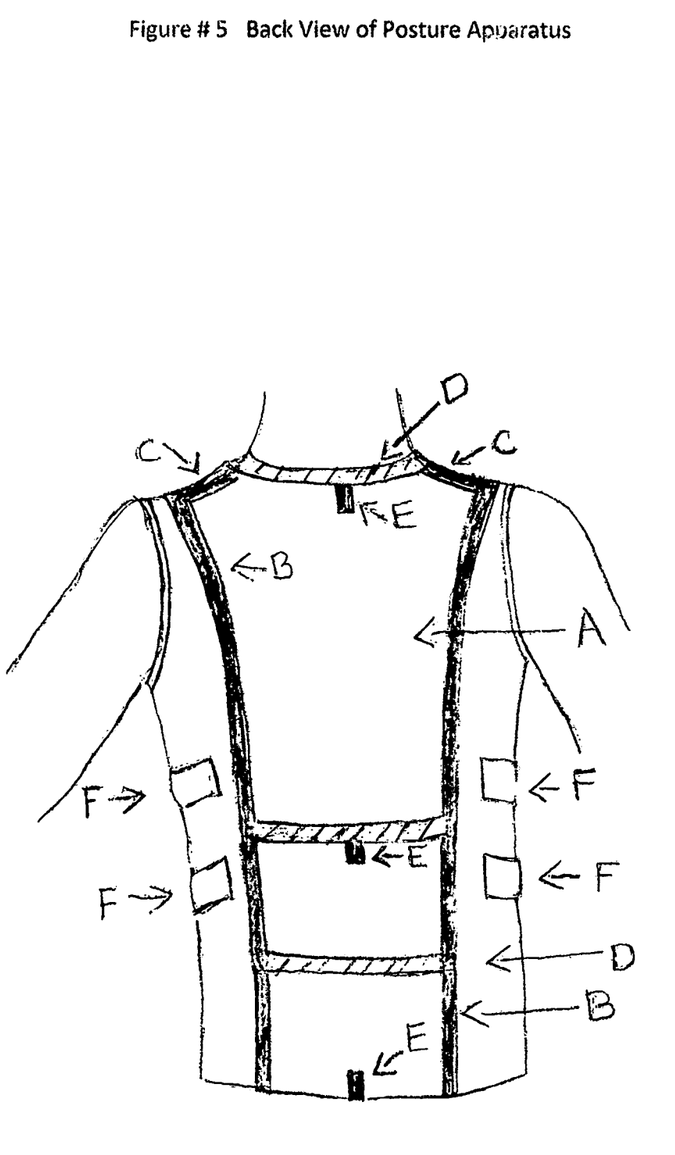
FIG. 5 is a back view that further comprises where the holding area (e.g. pockets, guides, etc.) with or without overlay material as illustrated in FIG. 4, is a self-contained attachment (A) to the Posture Improving Apparatus. The self-contained attachment perimeter (B) fastens to the Posture Improving Apparatus and (C) fastens to the front of the Posture Improving Apparatus. The self-contained Apparatus can also be put on a flat surface to be used. The self-contained attachment is one piece or (D) extension fasteners to cover entire length of spine. There are alignment markers and/or fasteners (E) to help with the placement of the self-contained attachment. And there are (F) side fasteners to enable adjustment for desired fit and attachment.
Figure 6:
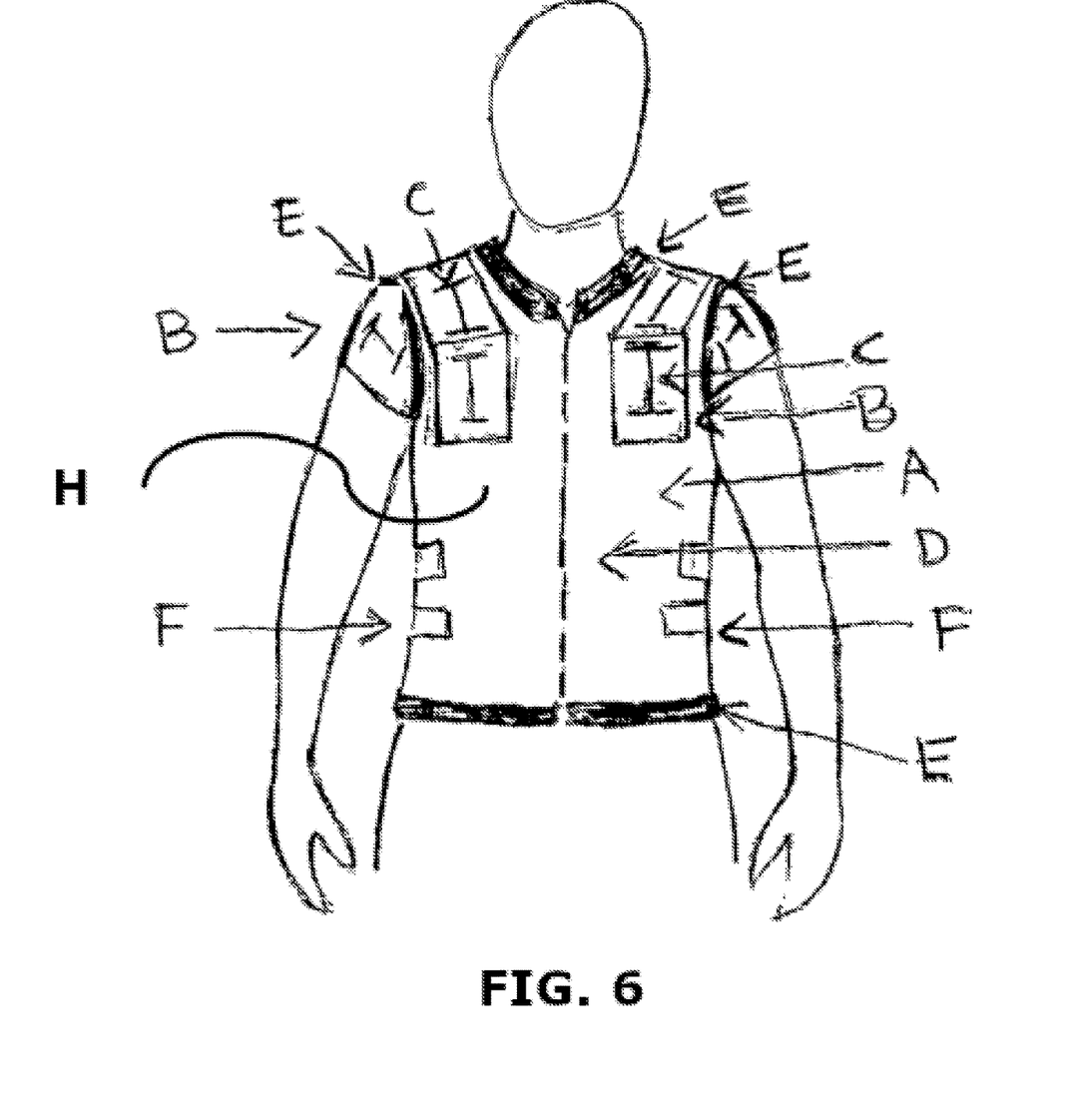
FIG. 6 Is a front view of the Posture Improving Apparatus (A) is illustrated in FIG. 6 as one piece from the neck down to the waist, with neck line options (e.g. crew, or v neck line, etc.). (B) is illustrating holding areas, (e.g. pockets, grooves, etc.). (C) is illustrating openings/closures for the filler, lifts, and inserts to be put into. (D) is illustrating front zipper/buttons, fasteners, etc. (E) is illustrating fasteners in different locations on the Posture Improving Apparatus (A) to have adjustable extensions (e.g. sleeves, neck, lower spine area, etc.). (F) is illustrating side fasteners used for adjustment for desired fit. (H) illustrating the front side of the apparatus.
Figure 7:
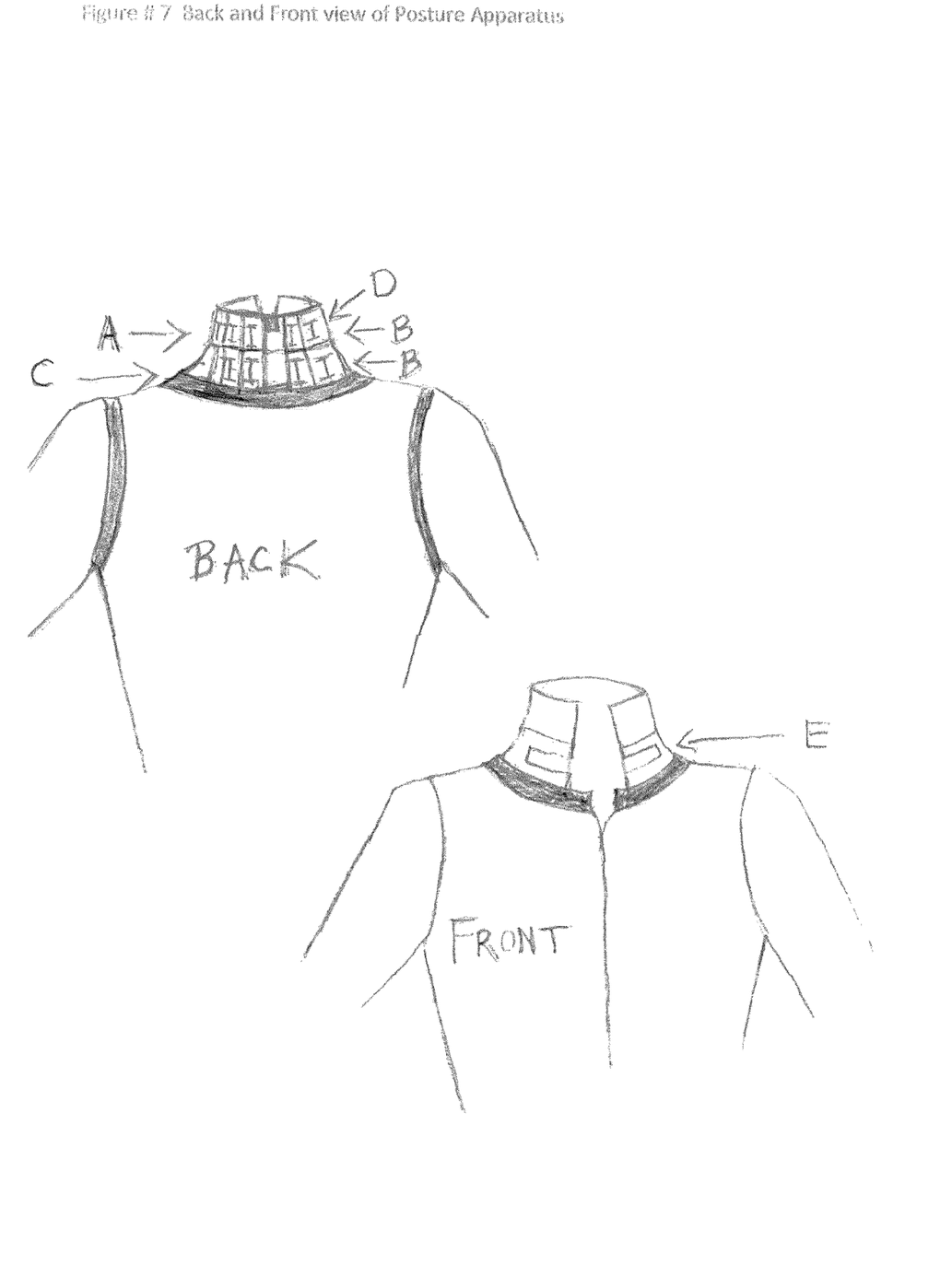
FIG. 7 Is a Front and Back view of the neck area of the Posture Improving Apparatus.
Figure 8:
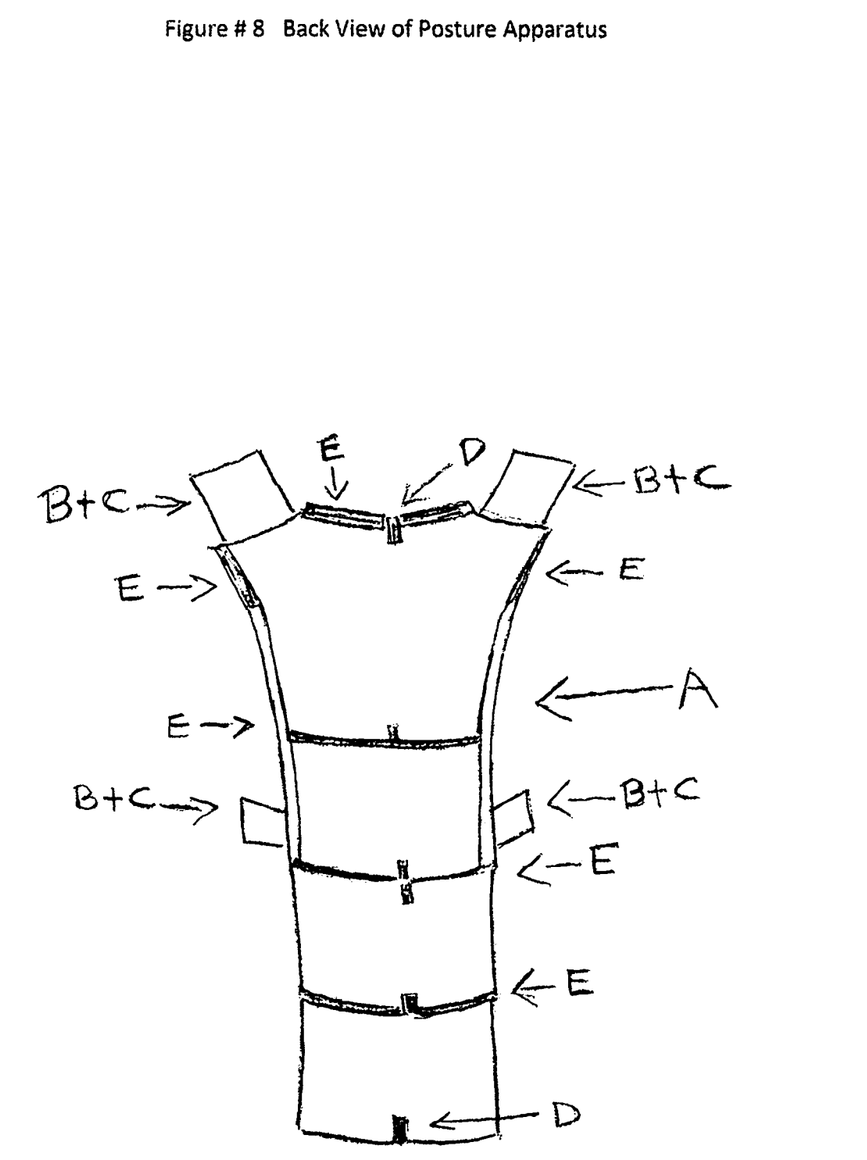
FIG. 8 Is a back view of an embodiment of the Posture Improving Apparatus that can be a separate stand alone, apparatus (e.g. bib type, etc.) (A) that can attach to the users own garment or can be put on a flat surface, and has all the embodiments and attributes described in FIG. 1-7. In this embodiment the posture apparatus is illustrated in FIG. 8 as one piece from the neck down to the end of the spine. (B) is illustrating fasteners to the users garment. These fasteners can be used for holding points on a flat surface. (C) is illustrating attachable and detachable fasteners to the users garment and/or a flat surface. (D) Illustrates alignment markers. (E) Illustrates the Posture Improving Apparatus fasteners for extensions.

Additional modifications and improvements of the present invention may also be apparent to those of ordinary skill in the art. Thus, the particular combination of parts described and illustrated herein is intended to represent only certain embodiments of the present invention, and is not intended to serve as limitations of alternative and/or derivative apparatus and/or device with the spirit and scope of the invention.

I claim:

1. A posture improving apparatus to be worn as a garment by a person to be used with the person lying supine on a flat surface for targeting specific areas of the person's body, lifting or modifying the specific areas in a manner wherein targeting other specific areas of the body to adjust and modify with assistance of gravity in response to the said lifting or modifying, and thereby facilitating the loosening and releasing of fascia tissue, connective tissue, muscles of the other specific areas, without direct use or creation of force or tension applied to the other specific areas;
    the posture improving apparatus comprising holding areas, wherein the holding areas are:
        removably attachable, adapted to be placed along length of the person's spine and width of the back of the person's body,
        selectively filled with filler, wherein filling attributes are determined for filling the holding areas, and where the filling attributes comprise the location and amount of holding areas that are to be filled, the type of filler, and size, width, depth, height, and length of filler, and wherein the filling attributes are selectable for a user, and wherein the fillers being comprised of at least one of firm material, flexible soft materials, formed materials, materials that maintain their shape, gel, air, and water,
        said fillers further being at least one of:
            an integral part of the apparatus,
            a separate attachable unit to the apparatus, and
            a self-contained unit of the apparatus;
    the posture improving apparatus having:
        gender neutral and flexible structure to offer freedom of movement to the user,
        extensions, attachment, overlays that are made of materials that hold their shape and form, with or without the use of fasteners, and that are soft or firm, and stretchable or non-stretchable materials.

2. The apparatus of claim 1 further comprising wherein, said holding areas are comprised of a first plurality of holding areas and a second plurality of holding areas with,
    said first plurality of holding areas contiguously disposed on the body at the back side and arranged such that said first plurality of holding areas adapted to fit along the spine between shoulder blades of the person under the mid and upper back extensor muscles,
    said second plurality of holding areas contiguously arranged on the body at the back side, adapted to lift within a region of the person's lower back when one or more of said holding areas of said second plurality of holding areas are filled with said filler.

3. The apparatus of claim 2, wherein the holding areas:
    are adapted to be filled up through openings/closures, wherein the opening and insert areas adapted to be opened vertically or horizontally;
    adapted to have flexible structural attributes comprising different shapes, dimensions, expandable and stretchable structure to allow various amounts, types, and dimensions of fillers to be filled inside the holding areas.

4. The apparatus of claim 3, the holding area having a pre-inserted filler having:
    predetermined types of filler; and/or
    predetermined locations or entire holding area filled up.

5. The apparatus of claim 4, the fillers adapted to adjust the width, height, and depth of the holding areas.

6. The apparatus of claim 4, wherein the fillers are comprised of self-contained packets that are placed inside the holding areas.

7. The apparatus of claim 4, wherein the apparatus having markers to determine whether the width of the holding area is equal to or lesser than width of said filler at a location at which the filler is to be placed.

8. The apparatus of claim 2 having air inflatable holding areas adapted to be pumped with an air pump, wherein the air pumped holding areas having closures and fasteners to keep the air in and to release the air out.

9. The apparatus of claim 2 the fillers are adapted to be self-contained air inflatable packets that are placed inside the holding area.

10. The apparatus of claim 2 having fasteners that open and close the apparatus, said fasteners adapted to tighten or loosen the apparatus.

11. The apparatus of claim 2, said apparatus configured to be worn on the person's body, and being: openable and closeable in the front or the apparatus configured to be pulled over the person's head.

12. The apparatus of claim 3, wherein said holding areas having, alignment markers and identification providing information and enabling utilization in relation to the location, location selection, choice, use, and anatomical information pertaining to the user.

13. A posture improving apparatus to be worn as a garment on a person, said garment comprising,
    a vest, said vest further comprising,
        means for holding lifts, fillers, weights, or inserts, said lifts, fillers, weights, or inserts being positioned to lift mid and/or upper back extensor muscles, while the person is lying supine,
        means for holding lifts, fillers, weights, or inserts, said lifts, fillers, weights, or inserts being positioned to lift the person's lower spine while the person is lying supine.

14. The posture improving apparatus of claim 13 wherein said means for lifting mid and/or upper back extensor muscles is comprised of a first plurality of holding areas said holding areas of said first plurality of holding areas contiguously disposed on the body at the back side and arranged such that said first plurality of holding areas adapted to fit along the spine between shoulder blades of the person under the mid and upper back extensor muscles, said holding areas of said first plurality selectively containing inserts adapted for specifically applying lifting force to the mid and/or upper back extensor muscles.

15. The posture improving apparatus of claim 14 wherein said means for lifting the person's lower spine further comprising a second plurality of holding areas contiguously arranged to lift the person's lower back, said holding areas of said second plurality selectively containing inserts adapted for specifically applying lifting force to the person's lower back.

16. A method using a vest for improving posture of a person comprising,
placing lifting inserts into holding areas of a first plurality of contiguously arranged holding areas on said vest, said lifting inserts adapted to be positioned so as to selectively lift mid and/or upper back extensor muscles of the person, said holding areas of said first plurality of holding areas adapted to be positioned between the person's shoulder blades along the person's spine,
lying in a supine position whereby said lifting inserts adapted to apply lifting force to the person's mid and/or upper back extensor muscles,
wherein said lifting of the person's mid and/or upper back extensor muscles causes relaxation of muscles and other tissues on the front and back of the person's body.

17. The method for improving posture of a person according to claim 16 further comprising,
placing lifting inserts into holding areas of a second plurality of contiguously arranged holding areas on said vest, said lifting inserts of said second plurality of holding areas positioned to selectively lift the persons lower back area, said second plurality of contiguously arranged holding areas arranged to cover the persons lower back area.

\* \* \* \* \*